United States Patent [19]

Phipps

[11] Patent Number: 5,057,072
[45] Date of Patent: Oct. 15, 1991

[54] IONTOPHORESIS ELECTRODE

[75] Inventor: Joseph B. Phipps, Plymouth, Minn.

[73] Assignee: Medtronic, Inc., Minneapolis, Minn.

[21] Appl. No.: 616,724

[22] Filed: Nov. 21, 1990

Related U.S. Application Data

[63] Continuation of Ser. No. 264,239, Oct. 28, 1988, abandoned.

[51] Int. Cl.[5] ............................................. A61N 1/30
[52] U.S. Cl. ................................... 604/20; 128/798; 424/449
[58] Field of Search ............... 604/20, 890.1; 128/783, 128/798, 802; 424/447, 448, 449

[56] References Cited

U.S. PATENT DOCUMENTS

| | | | |
|---|---|---|---|
| 4,051,002 | 9/1977 | Gunjima et al. | 204/98 |
| 4,250,878 | 2/1981 | Jacobsen et al. | 128/207.21 |
| 4,383,529 | 5/1983 | Webster | 604/20 |
| 4,416,274 | 11/1983 | Jacobsen et al. | 604/20 |
| 4,585,652 | 4/1986 | Miller et al. | 424/449 |
| 4,640,689 | 2/1987 | Sibalis | 604/20 |
| 4,720,334 | 1/1988 | DuBots et al. | 204/98 |
| 4,722,726 | 2/1988 | Sanderson et al. | 604/20 |
| 4,731,049 | 3/1988 | Parst | 604/20 |
| 4,744,787 | 5/1988 | Phipps et al. | 604/20 |
| 4,747,819 | 5/1988 | Phipps et al. | 604/20 |
| 4,752,285 | 6/1988 | Petelenz et al. | 604/20 |
| 4,756,710 | 7/1988 | Bondi et al. | 424/449 |
| 4,919,648 | 4/1990 | Sibalis | 604/20 |
| 4,921,475 | 5/1990 | Sibalis | 604/20 |
| 4,927,408 | 5/1990 | Haak et al. | 604/20 |

FOREIGN PATENT DOCUMENTS

| | | | |
|---|---|---|---|
| 203270 | 10/1985 | Japan | 604/20 |
| WO87/04936 | 8/1987 | PCT Int'l Appl. | |

OTHER PUBLICATIONS

Article entitled, "Noninvasive Delivery of a Novel Inotropic Catecholamine: Iontophoretic Versus Intravenous Infusion In Dogs", by John E. Sanderson et al., published in the *Journal of Pharmaceutical Sciences*, vol. 76, No. 3, Mar. 1987, pp. 215-218.

*Primary Examiner*—Stephen C. Pellegrino
*Assistant Examiner*—Ralph A. Lewis

[57] ABSTRACT

An improved iontophoresis electrode employing a current distributing member and a drug reservoir containing an ionic drug. The current distribution member is separated from the drug reservoir by means of a membrane or material selective for ions having a charge opposite to the charge of the ionic drug. The selective material is applied directly to the current distributing member.

39 Claims, 1 Drawing Sheet

IONTOPHORESIS ELECTRODE

This is a continuation of application(s) Ser. No. 07/264,239 filed on 10/28/88 now abandoned.

CROSS REFERENCE TO RELATED APPLICATIONS

Cross reference is made to applicant's concurrently filed, commonly assigned U.S. patent application entitled "IONTOPHORESIS ELECTRODE", Ser. No. 264,238, by Untereker et al, filed as of the date of this application. This application is hereby incorporated by reference in its entirety. Reference is also made to previously filed, commonly assigned U.S. patent application Ser. No. 154,566 entitled "IONTOPHORETIC DRUG DELIVERY", filed Feb. 10, 1988, by Untereker et al.

BACKGROUND OF THE INVENTION

This invention relates to methods and apparatus for transdermal medicament delivery and to improvements therein. More specifically, this invention relates to improved methods and apparatus for active (as opposed to passive) transdermal, ambulatory drug delivery. Yet more particularly, this invention relates to increasing the efficiency of iontophoresis devices and to improved methods of making and using such devices.

Recently, there has been a renewed interest in the technology of iontophoresis. Iontophoresis has been found to be useful in the transdermal administration or introduction of lidocaine hydrochloride, hydrocortisone, acetic acid, flouride, penicillin, dexamethasone sodium phosphate, and many other drugs. Perhaps the widest use of iontophoresis is the diagnosis of cystic fibrosis using pilocarpine nitrate iontophoresis.

In presently known iontophoresis devices, at least two electrodes are used. Both these electrodes are disposed so as to be in intimate electrical contact with some portion of the skin. The "active" electrode is the electrode from which the ionic drug is delivered into the body. The "indifferent" or ground electrode serves to close the electrical circuit through the body. A battery or other current source is coupled to the electrode to provide the electrical force to drive the drug into the body. For example, if the ionic substance to be driven into the body is positively charged, then the positive electrode (the anode) will be the active electrode and the negative electrode (the cathode) will serve to complete the circuit. If the ionic substance to be delivered is negatively charged, then the negative electrode will be the active electrode and the positive electrode will be the indifferent electrode. Of course, simultaneous delivery of drugs from both of the electrodes is also possible.

Generally, iontophoresis electrodes include a reservoir of the drug, typically compounded as a salt of the drug, for example a flouride or sulfate. These reservoirs may take the form of preformed gel bodies, such as disclosed in U.S. Pat. No. 4,382,529 issued to Webster, solid adhesive bodies as disclosed in U.S. Pat. No. 4,416,274, issued to Jacobson, or fluid reservoirs as disclosed in U.S. Pat. No. 4,250,878, issued to Jacobsen. Electrical current is typically applied to the fluid reservoir by means of a current distributing member, which may take the form of a metal plate, a foil layer, a conductive screen, or a dispersion of conductive particles within the drug reservoir.

Typically, the current distributing member in iontophoresis electrodes has been constructed of an inert material, such as stainless steel or platinum. However, more recently use of sacrificial current distributing members which are oxidized or reduced themselves during delivery of the drug has been discussed. Use of sacrificial current distributing members can avoid the pH changes and other adverse effects associated with the hydrolysis of water which generally accompanies the use of inert current distributing members. Electrodes with sacrificial current distributing members are disclosed in U.S. Pat. No. 4,744,787, issued to Phipps et al, incorporated herein by reference in its entirety. Such electrodes are also discussed in the above-cited copending application by Untereker et al, also incorporated herein by reference in its entirety.

An alternative approach to avoiding the adverse effects associated with hydrolysis of water at the current distributing member is disclosed in the published PCT Patent Application No. WO 87/04936, published Aug. 27, 1987, by Sanderson et al, corresponding to U.S. Pat. No. 4,722,726. This electrode system is also described in the article "Noninvasive Delivery of a Novel Inotropic Catecholamine: Iontophoretic Versus Intravenous Infusion in Dogs" by Sanderson et al, published in the *Journal of Pharmaceutical Sciences*, Vol. 76, No. 3, March 1987, pp. 215-218. In this electrode system, an inert current distributing member is used and the electrode is divided into an upper chamber filled with a buffer and a lower chamber containing the ionic drug. The upper chamber is separated from the lower chamber by means of an ion selective membrane. As described, it is apparently intended that the buffer solution in the upper chamber mitigate the effects of hydrolysis of water, and that the ion selective membrane isolate the drug from the contents of the upper chamber.

In electrodes including fluid reservoirs, as disclosed in U.S. Pat. No. 4,250,878 issued Jacobson, delivery of the drug typically takes place through a microporous membrane. Typically, such membranes are permeable based on size, and therefore must be permeable to any ion equal to or smaller than the drug ion intended to be delivered. In U.S. Pat. No. 4,640,689, issued on Feb. 3, 1987 to Sibalis, an iontophoresis electrode including a gel type drug reservoir provided with a semipermeable membrane is disclosed. This reference also suggests the use of an "ion selective retention gel" intermediate the drug reservoir and the semipermeable membrane. The ion to be retained by the gel is not discussed.

SUMMARY OF THE INVENTION

The present invention relates to an improvement to iontophoresis electrodes. The invention is especially beneficial when embodied in iontophoresis electrodes of the type employing sacrificial cathodes or anodes which are oxidized or reduced, respectively, during iontophoretic drug delivery. The use of such sacrificial current distributing members avoids electrolysis of water, as the materials chosen for the current distributing members are oxidized or reduced at a lower voltage than required to hydrolyze water. For example, the positive electrode (anode) may be silver and the negative electrode (cathode) may be silver/silver chloride. The invention is also believed beneficial when embodied in iontophoresis electrodes employing inert current distributing members.

In conjunction with such electrodes, the present invention supplies an improvement in the form of a coating of a cation or anion selective material applied directly to the current distributing member. A cation selective material would be applied to the current distributing member in the cathode (negative electrode) and an anion selective material would be applied to the current distributing member in the anode (positive electrode). This coating will prevent the migration of ions produced during the oxidation or reduction of a sacrificial current distributing member into the drug reservoir. In addition, the charge selective material prevents direct contact between the current distributing member and the drug ions in the reservoir. This minimizes electrochemical oxidation or reduction of the drug, and is believed beneficial in preventing drug degradation.

DETAILED DESCRIPTION OF THE INVENTION

Figure 1:
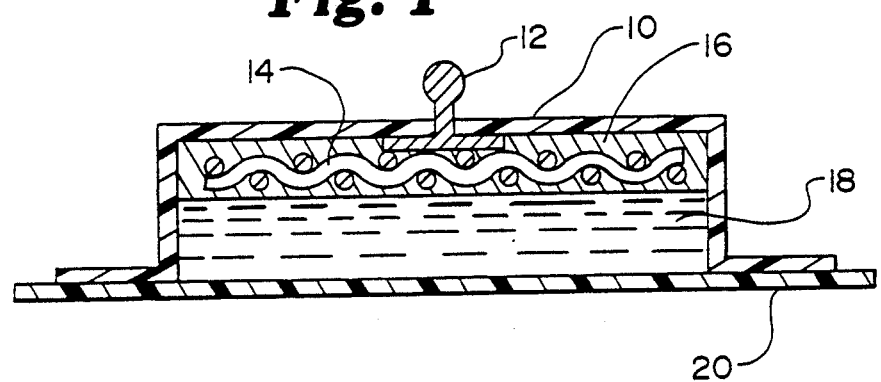
FIG. 1 shows a sectional view through an electrode according to the present invention.

FIG. 1 shows a sectional view through an active iontophoresis electrode according to the present invention. The electrode is provided with a housing 10, which may be fabricated of an insulative plastic, such as polyvinyl chloride or polyethylene. An electrical snap connector 12 extends from the top side of housing 10, and is electrically coupled to a screen 14 which serves as the current distribution member. Reservoir 18 contains the drug to be delivered which typically is either ionic drug or is readily ionizable within the reservoir. Screen 14 is preferably fabricated of a material which is reduced or oxidized at an electrical potential less than that required to hydrolyze water. Suitable examples are, for example, silver for the positive electrodes (anodes) and silver/silver chloride for the negative electrodes (cathodes). Alternatively, screen 14 may h=fabricated of an inert metal such as platinum or stainless steel.

Surrounding screen 14 is a material 16 which is permeable to ions having a charge opposite that of the drug in reservoir 18. For example, if the electrode is a positive electrode used to deliver a positively charged drug, material 16 would be an anion selective material. Conversely, if the electrode of FIG. 1 is the negative electrode, used to deliver a negatively charged drug, material 16 would be a cation selective material.

Examples of anionic and cationic selective membranes are described in the article "Acrylic Ion-Transfer Polymers", by Ballestrasse et al, published in the *Journal of the Electrochemical Society*, November 1987, Vol. 134, No. 11, pages 2745-2749. An additional appropriate anion exchange membrane would be a copolymer of styrene and divinyl benzene reacted with trimethylamine to provide an anion exchange membrane (see "Principles of Polymer Systems", by F. Rodriguez, *McGraw-Hill Book Co.*, 1979, pages 382-390). These articles are incorporated herein by reference in their entirety. An additional appropriate cationic permeable membrane for use in conjunction with delivery of a negatively charged drug would be a sulfonated styrene polymer or a sulfonated fluorocarbon polymer, e.g. Nafion TM membranes, a product of DuPont.

The provision of coating 16 has several important benefits. First, it prevents interaction of the ionic drug and the current distribution member during storage. This is believed beneficial in extending the shelf life of iontophoresis electrodes and makes possible combinations of drugs and current distribution members which might otherwise not provide an appropriate shelf life.

In the context of shelf life, providing the anion selective material 16 in direct contact with the current distribution member 14 is especially important. Although anion selective materials as discussed above select for negatively charged ions, positively charged ions will diffuse through them, over time, given the presence of a concentration gradient across the material. For example, the above cited Sanderson references suggest construction of an iontophoresis electrode in two chambers, the upper chamber containing the current distribution member being filled with a buffer solution, the lower chamber being filled with a drug solution, and an anion selective membrane provided intermediate the upper and lower chambers. Diffusion of positive ions from both the upper buffer chamber and the lower drug chamber would occur across the anion selective membrane would occur at a sufficient rate to severely limit the shelf life of such an electrode. This may require that the electrode be assembled shortly before use.

Because the electrode according to the present invention provides a charge selective material 16 directly applied to the current distributing member, diffusion of drug ions across the material should not occur in appreciable amounts. This allows for the electrode to be constructed in advance, while maintaining an extended shelf life.

In embodiments employing a sacrificial current distribution member, the provision of an ion selective coating is particularly advantageous. In use, a source of electrical current will be coupled to snap connector 12, and thereby to screen 14. Typically, such power supplies are constant current power supplies, and the voltage differential between screen 14 and drug reservoir 18 will thereby be determined by the voltage differential required to reduce or oxidize the material of screen 14.

If the drug to be delivered is a positive drug, for example lithium, screen 14 would be fabricated of a readily oxidizable material such as silver, material 16 would take the form of an anionic selective material, and the drug would preferentially be compounded with a counterion which reacts with ionic silver to form a neutrally charged compound. One example would be lithium chloride. When coupled to the power supply, screen 14 will be oxidized to produce silver ions. However, material 16 will subtantially reduce the migration of silver ions into the reservoir 18, where they might migrate in competition with the lithium ions. Instead, chlorine ions will migrate across an ion selective material 16, to form a silver chloride precipitate at the screen. This leaves lithium free to migrate with reduced competition from other positive ions.

If the drug to be delivered is a negatively charged ion, screen 14 would be fabricated of a readily reducible material, such as silver/silver chloride, material 16 would be a cationic selective material, and the drug in the reservoir would be compounded with a counter ion which forms a neutrally charged compound when combined with ionic chlorine. Examples of appropriate drug compounds would be copper or silver salicylate. In use, ionic silver in the silver chloride portion of screen 14 would be reduced, producing mobile chlorine ions. Cation selective material 16 would substantially reduce migration of chlorine ions into reservoir 18. Instead, positively charged copper or silver ions would migrate across material 16 to form a neutrally charged silver or copper chloride precipitate at screen 14. This leaves salicylate ion free to migrate with reduced competition from other negative ions.

This electrode construction provides significant additional advantages over prior art iontophoresis electrodes. For example, this construction reduces any toxic effects associated with the use of a silver current distribution member, and may make possible the use of materials such as a lead, which would otherwise be counterindicated. In addition, it allows the use of materials for current distribution member 14 which in their ionized state might otherwise react with the ionic drug in reservoir 18 during use of the electrode.

As noted above, the invention may be practiced in conjunction with inert current distributing members. This approach is particularly valuable in conjunction with the delivery of drugs which take the form of weak acids or weak bases. In these electrodes, hydrolysis of water is deliberately induced, with the hydrolysis product combining with the drug as compounded to produce an ionic, mobile species. For example, a weakly acidic drug D may be placed in a drug reservoir including a platinum current distributing member, which functions as the anode of the iontophoresis system. Hydrolysis of water occurs at the anode, with excess hydrogen ions combining with the drug to produce a charged species $DH^+$, which is substantially the only charged species within the reservoir. Corresponding systems employing weakly basic drugs may also be produced. Such systems are described in more detail in the above cited patent application Ser. No. 154,566, by Untereker et al, previously incorporated by reference.

As manufactured, it is anticipated that the drug reservoir 18 will take the form of a solid or semisolid gel. In this case, the release liner 20 would typically be provided to seal the drug reservoir 18 against contamination and to prevent the gel in reservoir 18 from drying out over time. Alternative embodiments of the invention may employ fluid drug reservoirs surrounded by semipermeable membranes.

Preferably, drug reservoir 18 is free of ionic or readily ionizable material other than the drug to be delivered. For example, the matrix may take the form of a polar, nonionic gel, such as a polyvinyl alcohol gel or a gel as disclosed in EPO Patent No. 0 060 451, issued on Sept. 17, 1986 to Lattin et al. This EPO patent is incorporated by reference herein in its entirety.

Figure 2:
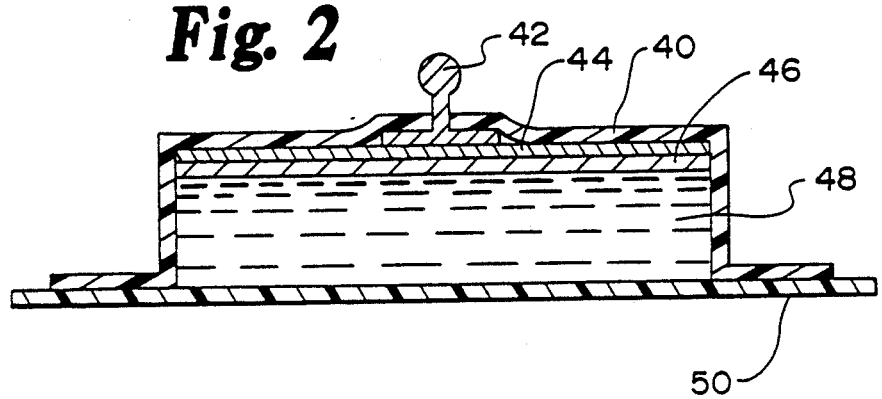
FIG. 2 shows a sectional view through a second embodiment of an electrode according to the present invention.

FIG. 2 is a sectional view of an alternative embodiment of an iontophoresis electrode according to the present invention. The electrode is provided with a housing 40, which may be fabricated of an insulative plastic, such as polyvinyl chloride or polyethylene. An electrical snap connector 42 extends from the top side of housing 40, and is electrically coupled to metallic foil 44 which serves as a current distribution member. Foil 44 may be fabricated of a material such as silver or silver chloride which is reduced or oxidized at an electrical potential less than required to hydrolize water, or may be an inert metal such as platinum or stainless steel. An ion selective material 46 is applied as a coating or layered directly over foil 40, and serves the same function as the ion selective material 16, discussed in conjunction with FIG. 1. The iontophoretic drug for delivery is contained within reservoir 48, which will take the form of a solid or semisolid gel in the preferred embodiment. A release liner 50 is provided to seal the drug reservoir 48 against contamination and to prevent the reservoir 18 from drying out over time.

Figure 3:
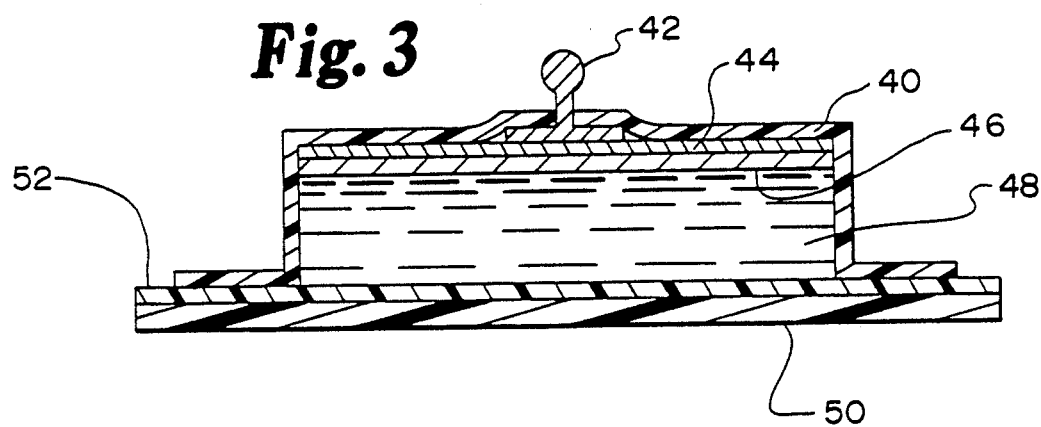
FIG. 3 shows a sectional view through an embodiment of an electrode according to the present invention which is a variation of the embodiment shown in FIG. 2.

An electrode according to the present invention may also employ a charge selective ion permeable membrane 52 at the interface of the drug reservoir and the skin, as disclosed in the above cited patent application entitled "IONTOPHORESIS ELECTRODE" by Untereker et al and shown in FIG. 3 hereof. FIG. 3 is a showing of an embodiment similar to that of FIG. 2 with the elements similarly numbered but having an additional element 52 which is a charge selective ion permeable membrane attached to housing 40 as shown so as to be positioned at the interface of drug reservoir 48 and the skin when the electrode is used after release liner 50 has been removed. In such case, the membrane applied between the reservoir and the skin would selectively pass ions having the charge of the ionic drug to be delivered.

In connection with the above specification, I claim:

1. An iontophoresis electrode comprising:
   a conductive, current distributing member;
   means for coupling said current distributing member to a source of electrical current;
   reservoir means containing an ionic or ionizable drug to be delivered, and being further constructed and arranged to be in electrical contact with the current distributing member; and
   a layer of charge selective material applied directly to said current distributing member, and arranged intermediate said current distributing member and said reservoir means and coupling them together.

2. An iontophoresis electrode, comprising:
   a current distributing member fabricated of a material which is readily oxidized or reduced at a voltage less than the voltage required to hydrolyze water;
   connector means for connecting said current distributing member to a source of electrical current;
   reservoir means constructed and arranged for the delivery of drug to skin against which the electrode is contacted, said reservoir means being coupled to said current distributing member, said reservoir means containing an ionic drug compounded with a counterion which reacts with said material of which said current distributing member is fabricated, after said material is oxidized or reduced, to produce a compound insoluble with said reservoir means; and
   a layer of charge selective material applied directly to said current distributing member, said material selective for ions of the opposite charge as said ionic drug, said material applied intermediate said current distributing member and said reservoir means and coupling them together.

3. An iontophoresis electrode for delivery of an ionic or ionizable drug to a skin comprising:
   a conductive, current distributing member;
   means for coupling said current distributing member to a source of electrical current;
   reservoir means containing an ionic or ionizable drug to be delivered to said skin, the reservoir means being constructed and arranged for delivery of the drug to skin against which the electrode is contacted;
   a layer of first charge selective material applied directly to said current distributing member and contacting the reservoir means whereby the current distributing member and reservoir means are coupled together; and a second charge selective material located at the interface of the drug reservoir means and the skin, the second charge selective material selectively passing ions having the charge of the drug to be delivered to said skin from the reservoir means.

4. The electrode of claim 1, 2 or 3, wherein the drug to be delivered is cationic or ionizable into cations and the charge selective material is selectively permeable to anions.

5. The electrode of claim 4, wherein the charge selective material applied directly to the current distributing member comprises an anion exchange membrane.

6. The electrode of claim 5, wherein the anion exchange membrane is selected from the group consisting of copolymers of styrene and divinyl benzine reacted with trimethylamine.

7. The electrode of claim 1, 2 or 3, wherein the drug to be delivered is anionic or ionizable into anions and the charge selective material applied directly to the current distributing member is selectively permeable to cations.

8. The electrode of claim 7, wherein the charge selective material applied directly to the current distributing member comprises a cation exchange membrane.

9. The electrode of claim 8, wherein the cation exchange membrane is selected from the group consisting of sulfonated styrene polymers and sulfonated fluorocarbon polymers.

10. The electrode of claim 1 or 3, wherein the current distributing member is comprised of an inert metal.

11. The electrode of claim 10, wherein the inert metal is selected from the group consisting of platinum and stainless steel.

12. The electrode of claim 10, wherein the drug is selected from weak acids and weak bases.

13. The electrode of claim 2, wherein the drug to be delivered is cationic or ionizable into cations and the current distributing member comprises a material which is oxidizable.

14. The electrode of claim 13, wherein the oxidable material comprises silver.

15. The electrode of claim 14, wherein the counterion comprises chloride and the insoluble compound comprises silver chloride.

16. The electrode of claim 2, wherein the drug to be delivered is anionic or ionizable into anions and the current distributing member comprises a material which is reducible.

17. The electrode of claim 16, wherein the reducible material comprises silver/silver chloride.

18. The electrode of claim 17, wherein the counterion is capable of forming a neutrally charged compound when combined with ionic chlorine.

19. The electrode of claim 18, wherein the counterion is selected from the group consisting of copper and silver.

20. The electrode of claim 1, 2 or 3, wherein the reservoir means comprises a nonionic gel.

21. A method of fabricating an iontophoresis electrode, comprising the steps of:

selecting an ionic or ionizable drug to be delivered;
including said drug within a reservoir means through which said drug is permeable for delivery to skin against which the electrode is contacted;
selecting a conductive current distributing member;
selecting a charge selective material selectively permeable to ions of the charge opposite to that of said drug; and
assembling said electrode by applying said charge selective material directly to said current distributing member and mounting said current distributing member to said reservoir such that said charge selective material is located intermediate said current distributing member and said reservoir.

22. A method of fabricating an iontophoresis electrode, comprising the steps of:

selecting an ionic drug to be delivered:
selecting a sacrificial current distributing member fabricated of a material readily oxidizable or reducible by application of a voltage less than required to hydrolyze water;
compounding said ionic drug with a counterion which will react with the material of which said current distributing member is fabricated, after said material is oxidized or reduced, to form a neutral compound, and placing said compounded ionic drug into a reservoir means through which said ionic drug is permeable for delivery to skin against which the electrode is contacted; and
applying a charge selective material directly to said current distributing member, said charge selective material permeable to ions having the charge opposite to the charge of said ionic drug, said charge selective material applied between said current distributing member and said reservoir.

23. The method of claim 3 or 22, wherein the drug to be delivered is cationic or ionizable into cations and the charge selective material is selectively permeable to anions.

24. The method of claim 23, wherein the charge selective material applied directly to the current distributing member comprises an anion exchange membrane.

25. The method of claim 24, wherein the anion exchange membrane is selected from the group consisting of copolymers of styrene and divinyl benzene reacted with trimethylamine.

26. The method of claim 3 or 22, wherein the drug to be delivered is anionic or ionizable into anions and the charge selective material applied directly to the current distributing member is selectively permeable to cations.

27. The method of claim 26, wherein the charge selective material applied directly to the current distributing member comprises a cation exchange membrane.

28. The method of claim 27, wherein the cation exchange membrane is selected from the group consisting of sulfonated styrene polymers and sulfonated fluorocarbon polymers.

29. The method of claim 3, wherein the current distributing member is comprised of an inert metal.

30. The method of claim 29, wherein the inert metal is selected from the group consisting of platinum and stainless steel.

31. The method of claim 29, wherein the drug is selected from weak acids and weak bases.

32. The method of claim 22, wherein the drug to be delivered is cationic or ionizable into cations and the current distributing member comprises a material which is oxidizable.

33. The method of claim 32, wherein the oxidizable material comprises silver.

34. The method of claim 33, wherein the counterion comprises chloride and the insoluble compound comprises silver chloride.

35. The method of claim 22, wherein the drug to be delivered is anionic or ionizable into anions and the current distributing member comprises a material which is reducible.

36. The method of claim 35, wherein the reducible material comprises silver/silver chloride.

37. The method of claim 36, wherein the counterion is capable of forming a neutrally charged compound when combined with ionic chlorine.

38. The method of claim 37, wherein the counterion is selected from the group consisting of copper and silver.

39. The method of claim 3 or 22, wherein the reservoir means comprises a nonionic gel.

* * * * *